United States Patent
Saini (10) Patent No.: US 7,387,720 B2
(45) Date of Patent: Jun. 17, 2008

(54) ELECTROLYTIC METHOD AND APPARATUS FOR TRACE METAL ANALYSIS

(75) Inventor: Harmesh K. Saini, Santa Clara, CA (US)

(73) Assignee: Metara, Inc., Sunnyvale, CA (US)

(*) Notice: Subject to any disclaimer, the term of this patent is extended or adjusted under 35 U.S.C. 154(b) by 767 days.

(21) Appl. No.: 10/836,913

(22) Filed: Apr. 30, 2004

(65) Prior Publication Data

US 2005/0241956 A1 Nov. 3, 2005

(51) Int. Cl.
*G01J 3/00* (2006.01)

(52) U.S. Cl. .................... 205/705; 205/714

(58) Field of Classification Search ........... 205/705, 205/714

See application file for complete search history.

(56) References Cited

U.S. PATENT DOCUMENTS

| | | | |
|---|---|---|---|
| 4,123,336 A | 10/1978 | Seko et al. | |
| 4,279,712 A | 7/1981 | Satoh et al. | |
| 4,322,270 A | 3/1982 | Skala | |
| 4,663,006 A | 5/1987 | Yao et al. | |
| 4,790,918 A | 12/1988 | Bridger et al. | |
| 5,372,717 A | 12/1994 | Abolt et al. | |
| 5,855,757 A | 1/1999 | Sivilotti | |
| 6,113,773 A | 9/2000 | Shimamune et al. | |
| 6,228,651 B1 | 5/2001 | Fukuda et al. | |
| 2004/0046121 A1* | 3/2004 | Golden et al. | 250/339.07 |

OTHER PUBLICATIONS

C. Belmont et al., "Coplanar interdigitated band electrodes for electrosynthesis. Part 4: Application to sea water electrolysis", Electrochimica Acta 44, 1998, pp. 597-603.

Rodnei Bertazzoli et al., "Electrolytic Removal of Metals Using a Flow-Through Cell with a Reticulated Vitreous Carbon Cathode", J. Braz. Chem. Soc., 1997, 487-493, vol. 8, No. 5.

Gary J. Van Berkel, "Electrolytic deposition of metals on to the high-voltage contact in an electrospray emitter . . . ", J. Mass Spec, 2000, 773-783, 35.

Werner Kern, ed., "Handbook of Semiconductor Wafer Cleaning Technology", 1993, 19-21, Noyes Pub., Westwood NJ.

* cited by examiner

*Primary Examiner*—Arun S. Phasge
(74) *Attorney, Agent, or Firm*—Jonathan W. Hallman; MacPherson Kwok Chen & Heid LLP (57) ABSTRACT

An electrolytic method and apparatus for treating a solution sample allowing for the accurate and substantially real-time and on-line analysis of trace contaminants in the solution sample. The method of the present invention includes two stages. The solution sample is electrolyzed during a first stage to decompose the matrix, thereby substantially neutralizing the matrix, while during a second stage deposited or precipitated metals are recovered and/or stabilized in solution. An apparatus for carrying out the method is also disclosed.

27 Claims, 10 Drawing Sheets

(Not Drawn to Scale)

```
Pgm 101   PRINT    "Electrolysis Polarity Cycling with Delay 031022\n"

SLEW 0
          DELAY 1000
          SET Pos = 0

SET Stall = false
          PRINT "Ready..."
          PRINT "Input Polarity Switch Count"
          INPUT ncycles
          PRINT "Input Polarity Switching Delay Time in Seconds"
          INPUT sdelay
          PRINT "Input Settling Time Delay in Seconds"
          INPUT sdlyl
          SET etime = 0
          SET ctotal = ncycles
    LBL   SW1
          BR SW2, Io 31 = 1
          SET Io 34 = 0
          DELAY 1000*sdlyl
          SET    Io 31 = 1
          DELAY 1000*sdlyl
          SET Io 34 = 1
          BR RTRN
    LBL   SW2
          SET Io 34 = 0
          DELAY 1000*sdlyl
          SET    Io 31 = 0
          DELAY 1000*sdlyl
          SET Io 34 = 1
          BR RTRN
    LBL   RTRN
          DELAY 1000*sdelay
          DEC ncycles
          SET ttmp = sdelay+sdlyl+sdlyl+etime
          SET etime = ttmp
          SET etmin = etime/60
          SET cdone = ctotal-ncycles
          PRINT "Complet ",cdone," cyc of ",ctotal," elapsed time = ",etmin,"(min)"
          BR SW1, ncycles>0
          SET Io 34 = 0 'turn power off
          PRINT "Polarity Change End"
          END
                                                            Pgm
```

ELECTROLYTIC METHOD AND APPARATUS FOR TRACE METAL ANALYSIS

BACKGROUND OF THE INVENTION

1. Field of Invention

The present invention generally relates to analysis of solutions. More particularly, the present invention relates to online automated matrix elimination and trace contaminant analysis of process chemical solutions.

2. Discussion of the Related Art

Chemical solutions are used in various manufacturing processes in a multitude of industries, including the semiconductor, environmental, and pharmaceutical industries. A solution sample includes a matrix, defined herein as a liquid solution, suspension, or colloid, and may or may not include a detectable amount of at least one analyte of interest. Examples of matrixes are diluted or concentrated acids, bases, oxidants, reducing reagents, solvents (such as alcohols, esters, ethers, glycols, ketones, amides, amines, or their mixtures), cleaning solutions, photoresists, strippers, and developers. Examples of analytes of interest are metals and their species.

The matrix of a solution sample has a pronounced effect on the quantification of trace constituents by modern analytical instruments. For example, a common problem is detecting analytes of interest in a matrix including one or more compounds of high ionic strength. Many times, the desired analyte peaks or signals are obscured by the large interfering peak of a matrix ion. In many analytical instruments, the detector is saturated with matrix ion signals and is not able to distinguish the desired analyte signal.

In some cases, the desired signal is suppressed because the matrix ions compete with the desired analyte ions when ionization of the sample occurs for analysis purposes. For example, during ion formation in electrospray ionization, the matrix ions can solvate or deprotonate the analyte of interest resulting in less ion formation of the analyte of interest.

The composition or properties of a matrix may also change from process to process and during the life of the sample, which may then affect the recovery of an analyte from a complex matrix. Analyte speciation may further compound this effect. The stability of a sample/analyte may also change during analysis because of a changing thermal regime or photolytic effect. Thus, inaccurate analysis of a sample may occur because of the transitory nature of the matrix.

In many instances, however, accurately monitoring the analytes of a sample at a specific point in time during a process is highly desirable. For example, in semiconductor manufacturing processes, monitoring the metallic impurities in a cleaning solution is of immense importance for producing reliable devices with high yield. Purity of these solutions during offline and online processes is very important as well.

Reliably measuring the metallic contaminants in a cleaning solution at a parts-per-trillion level, especially in the presence of a high matrix, is not only complicated but also laborious and time consuming. For example, a solution of hydrochloric acid (HCl), hydrogen peroxide ($H_2O_2$), and water in varying ratio may be used to remove the metallic residues from the surface of a silica wafer by forming chloride complexes and dissolving in the solution. The solution is commonly known as a Standard Clean 2 solution (SC2). The most common ratio for SC2 used in semiconductor manufacturing is one part of 37% HCl to one part of 30% $H_2O_2$ to six parts of ultra pure water (UPW).

The continuous decrease in the geometry of devices requires increased control of the contaminants in a solution such as SC2. Control over the contaminants is important because SC2 comes in direct contact with the electronic circuitry during device fabrication. Thus, the quantitative determination of metallic contaminants in fresh and spent SC2 solution is of immense importance, for example in determining the cause of a defect or the endpoint of a process.

Due to the high matrix of chloride ions in SC2, the simultaneous online determination of trace levels of many metals is very difficult. In the absence of an analytical instrument that can monitor online all the contamination levels of metals in SC2, it is common practice to collect the SC2 sample before, during, and/or after a process of interest and to send the samples to an offline analytical laboratory for analysis. Typically, it takes between 4 to 24 hours before the analysis results are received by process personnel. Accordingly, in most cases, if a problem is detected, such as impurities in the SC2, processing of defective product will have occurred for some time and the cost related to low yield will be high.

Another problem with offline analysis is maintaining the integrity of the SC2 sample starting from collection to the end of analysis. First, SC2 cleaning is typically done at elevated temperatures, between about 60° C. to about 75° C., and at this temperature the matrix of SC2 is dynamic in nature such that the components of the SC2 are continually reacting with other components and can change over time. Thus, by the time the sample reaches a laboratory for analysis, the sample may not be in a representative formulation as it was at the time of collection. Second, the SC2 matrix is a strong absorption media for airborne soluble contaminants such that if samples are exposed to air at any stage during sampling, transportation, or analysis, the matrix of the sample may be altered or contaminated. Third, the cleanliness of the sampling containers is important and a large amount of time and money is spent on cleaning sampling containers. The amount of time the sample is allowed to sit in the sampling container before being analyzed can also affect the analysis outcome. It has been reported that even the cleanest of sampling containers can leach out many undesirable contaminants. Fourth, offline elimination, neutralization, or modification of matrixes generally poses a high risk of contamination that can affect the integrity of the sample for the reasons stated above.

Depending on the nature and concentration of the SC2 matrix, various analytical laboratories have developed their own methods to test a sample including an SC2 matrix. For example, some laboratories dilute the sample to reduce the effect of the matrix but by doing so many ultra low trace level contaminants may not be detected. Other laboratories eliminate the matrix by heat and/or evaporation but by doing so potentially lose the integrity of the sample constituents.

As a result, many semiconductor device manufacturers are in need of online measurements to provide substantially real-time analysis. Therefore, a method and apparatus for accurate online elemental and molecular analysis of process solutions, such as SC2, on a substantially real-time basis are highly desirable.

SUMMARY

The present invention provides an online electrolytic method and apparatus for preparing a sample for analysis by treating process chemical matrixes, allowing for the accurate and substantially real-time analysis of trace contaminants in a process solution sample. The method of the present invention includes two stages. The solution sample is electrolyzed during a first stage to decompose the matrix, thereby substantially eliminating or neutralizing the matrix, while during a second stage deposited or precipitated metals are recovered and/or stabilized in solution by repeatedly reversing the polarity of the electrodes.

In accordance with one embodiment of the present invention, a method of analyzing trace metals in solution is provided, including providing a first electrode and a second electrode in a reservoir, and providing a sample in the reservoir so that the sample is in contact with the first and second electrodes, the sample including a matrix and at least one trace metal to be analyzed. The method further includes applying a first stage voltage to the first electrode and applying a first stage voltage of opposite polarity to the second electrode, wherein the polarity of the first stage voltages are repeatedly reversed at a first time interval and for a first number of cycles to thereby decompose the matrix. A second stage voltage is then applied to the first electrode and a second stage voltage of opposite polarity is applied to the second electrode, wherein the polarity of the second stage voltages are repeatedly reversed at a second time interval and for a second number of cycles to thereby recover and/or stabilize the at least one trace metal in solution for subsequent analysis.

In accordance with another embodiment of the present invention, a method of analyzing trace metals in solution includes providing a first electrode, a second electrode, and a third electrode in a reservoir, and providing a sample in the reservoir so that the sample is in contact with the first, second, and third electrodes, the sample including a matrix and at least one trace metal to be analyzed. The method further includes applying a first stage voltage to the first electrode and applying a first stage voltage of opposite polarity to the second electrode, wherein the polarity of the first stage voltages are repeatedly reversed at a first time interval and for a first number of cycles to thereby decompose the matrix. Then a second stage voltage is applied to the first and second electrodes and a second stage voltage of opposite polarity is applied to the third electrode to thereby recover and/or stabilize the at least one trace metal in solution for subsequent analysis.

In accordance with yet another embodiment of the present invention, an apparatus for analyzing trace metals in solution is provided, including a sampling device that provides a sample including a matrix and at least one trace metal to be analyzed, and an electrolytic apparatus operably coupled to the sampling device, wherein the electrolytic apparatus includes a reservoir for receiving the sample. The apparatus further includes a first electrode and a second electrode in contact with the sample, a polarity switching apparatus operably coupled to the first and second electrodes, wherein the polarity switching apparatus is capable of applying voltages of opposite polarity to the first and second electrodes. An analyzer is operably coupled to the electrolytic apparatus for analyzing the at least one trace metal in the sample.

Advantageously, the present invention provides an efficient and highly accurate method and apparatus for detecting trace contaminants in a solution sample. In particular, the present invention is highly advantageous when attempting to detect trace metal contaminants in an interfering matrix environment, thereby allowing for and/or greatly enhancing analysis.

These and other features and advantages of the present invention will be more readily apparent from the detailed description of the embodiments set forth below taken in conjunction with the accompanying drawings.

BRIEF DESCRIPTION OF DRAWINGS

Use of the same or similar reference symbols in different figures indicates identical or similar items. It is further noted that the drawings may not be drawn to scale.

DETAILED DESCRIPTION

The present invention uses the principles involved in a technique known as "electrolysis". Electrolysis is the method where electric potential is applied to a conductive solution and charged species migrate toward the oppositely charged electrode. Negatively charged and chemically active ions (anions) migrate toward the positively charged anode and are oxidized at the electrode surface. Positively charged ions (cations) migrate toward the negatively charged cathode and are reduced at the electrode surface. For example, during the electrolysis of sodium chloride ($Na^+Cl^-$), the negatively charged chloride ions ($Cl^-$) migrate toward the anode and are oxidized to chlorine gas, while the positively charged sodium ions ($Na^+$) migrate toward the cathode and are reduced to sodium metal.

Although electrolysis is a very efficient, fast, and clean technique to decompose or neutralize many highly concentrated matrixes (e.g., in SC2, the chloride ion matrix is oxidized to chlorine gas), the technique has not been previously used to detect trace metals in solution because the metals have tended to precipitate out of solution or have been deposited at the cathode surface. During conventional electrolysis, hydroxide ions (OH⁻) are produced at the cathode electrode and migrate into the solution sample where they react with metals to form salts that may precipitate out of solution. For example, most of the transition metals tend to form insoluble metal-oxide (MO) or metal-hydroxide (MOH) precipitates.

The present invention allows for trace metals analysis by treating the matrix and stabilizing the metals in solution. In one example, to analyze metallic contaminants in SC2, two electrolysis stages are performed. First, the high concentration of chloride ions matrix is oxidized to chlorine gas while second, the metals are maintained in solution.

Figure 1:
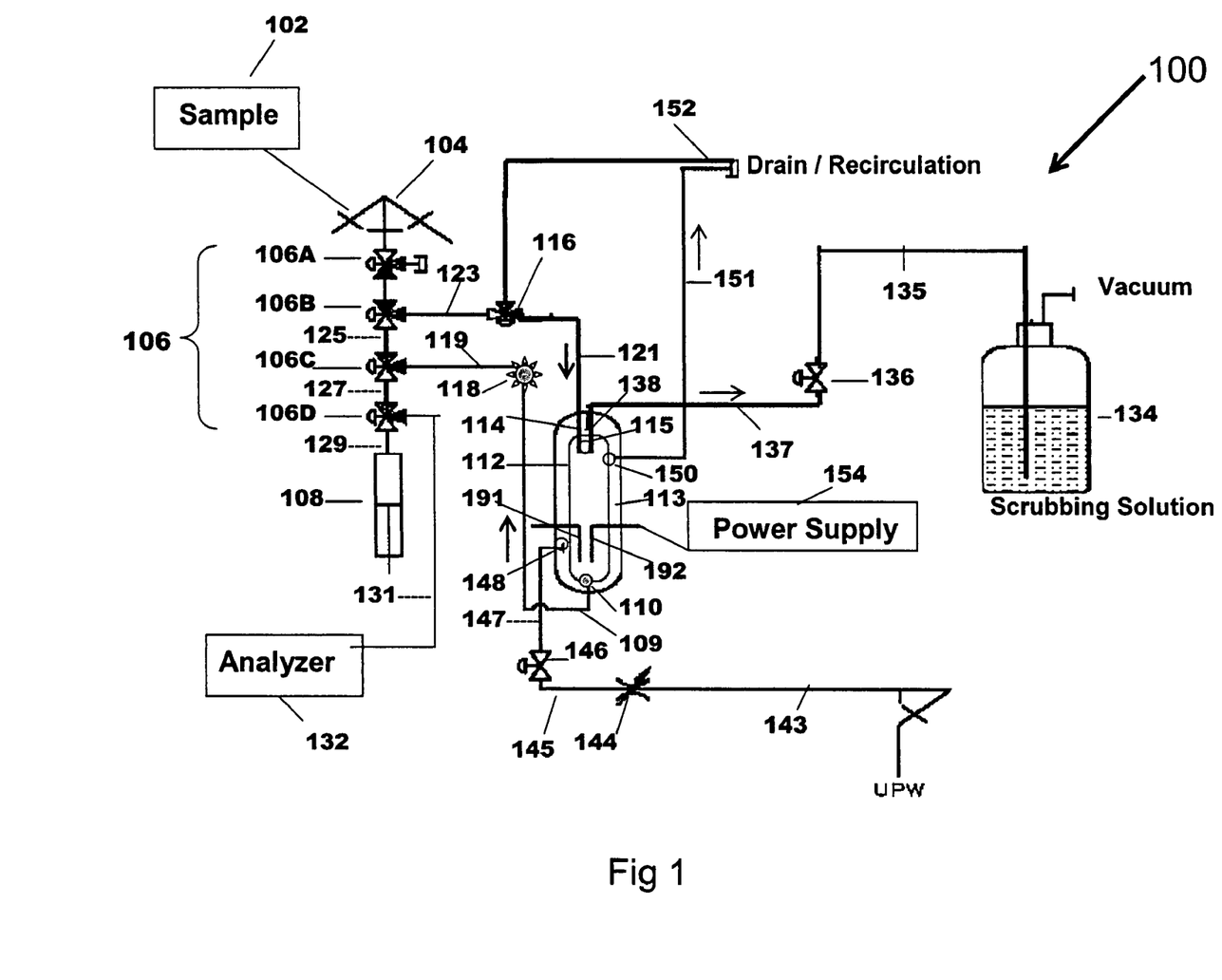
FIG. 1 shows a diagram illustrating an apparatus for analyzing trace metals, in accordance with one embodiment of the present invention.

FIG. 1 shows a diagram illustrating an apparatus 100 for analyzing trace metals in accordance with one embodiment of the present invention. A sample is extracted from a process wet bath (not shown) by a sampling apparatus 102, which can include a variable speed syringe in one example.

In one embodiment of the present invention, the solution sample is extracted after the solution sample has been mixed with appropriate isotope mixtures or other internal standards which can be used to achieve calibrated mass spectrometry measurements, as disclosed in co-pending and commonly assigned U.S. patent application Ser. No. 10/004,627, which is incorporated by reference herein for all purposes.

In other embodiments, the sample may be extracted without an isotope spike and the matrix of the sample is eliminated, neutralized, and/or modified and the metals stabilized in solution in accordance with the present invention.

Referring again to FIG. 1, the extracted sample is provided by sampling apparatus 102 into mixing tee 104, then drawn through valve stack 106 including valves 106A, 106B, 106C, and 106D, and loaded into variable speed syringe 108.

Valve 106B is then positioned to allow syringe 108 to provide the sample into an electrolytic apparatus 112 via line 129, valve 106D, line 127, valve 106C, line 125, valve 106B, line 123, valve 116, and line 121, passing through sample input port 115 of electrolytic apparatus 112. In one embodiment, electrolytic apparatus 112 includes two electrodes 191 and 192 coupled to a polarity switching apparatus 154 such that the sample passes through electrolytic apparatus 112 undergoing electrolysis and recovery of metals. Methods of electrolysis and metals recovery will be explained in greater detail below in conjunction with FIGS. 5 and 7. The matrix-treated sample then exits through sample output port 110 and is transported to syringe 108 through line 109, a fluid sensor 118, line 119, valve 106C, line 127, valve 106D, and line 129.

Finally, valve 106D is positioned to allow syringe 108 to provide the treated sample into an analyzer 132, which can detect trace contaminants in the sample, via line 129, valve 106D, and line 131.

Fluid sensor 118 controls the movement of syringe 108 and is used to determine any change in the sample volume and resultant change in the required stroke on syringe 108 when drawing treated sample back to itself. Fluid sensor 118 sends a signal to syringe 108 to stop pulling the sample when air passes through the sensor. Based upon the position of syringe 108, software is able to calculate the volume of the treated sample. The flow of sample from syringe 108 to electrolytic apparatus 112 and back to syringe 108 constitutes one sample treatment cycle. In one example, with no intent to limit the invention thereby, fluid sensor 118 includes a digital fiber sensor, part number FX-301-F, available from Powermatic Associates of Pleasanton, Calif.

In one example, with no intent to limit the invention thereby, variable speed syringe 108 is computer-controlled and includes a stepper motor controlled syringe with a KEL-F piston, Teflon syringe barrel, and fluorocarbon seals.

In one example, with no intent to limit the invention thereby, valve stack 106 including valves 106A, 106B, 106C, and 106D, is made up of valves having part number CASY-1427-03, available from Bay Advanced Technology of Menlo Park, Calif.

In one example, with no intent to limit the invention thereby, three-way valve 116 is a commercially-available valve having part number PV-1-2312, also available from Bay Advanced Technology of Menlo Park, Calif.

In one example, with no intent to limit the invention thereby, mixing tee 104 is made of Kel-F and Y-shaped to provide sufficient mixing of input solutions without leaching of contaminants. However, various mixing tees are applicable such as those that provide sufficient mixing, cleanliness, and compatibility with various solutions.

Figures 2A, 2B:
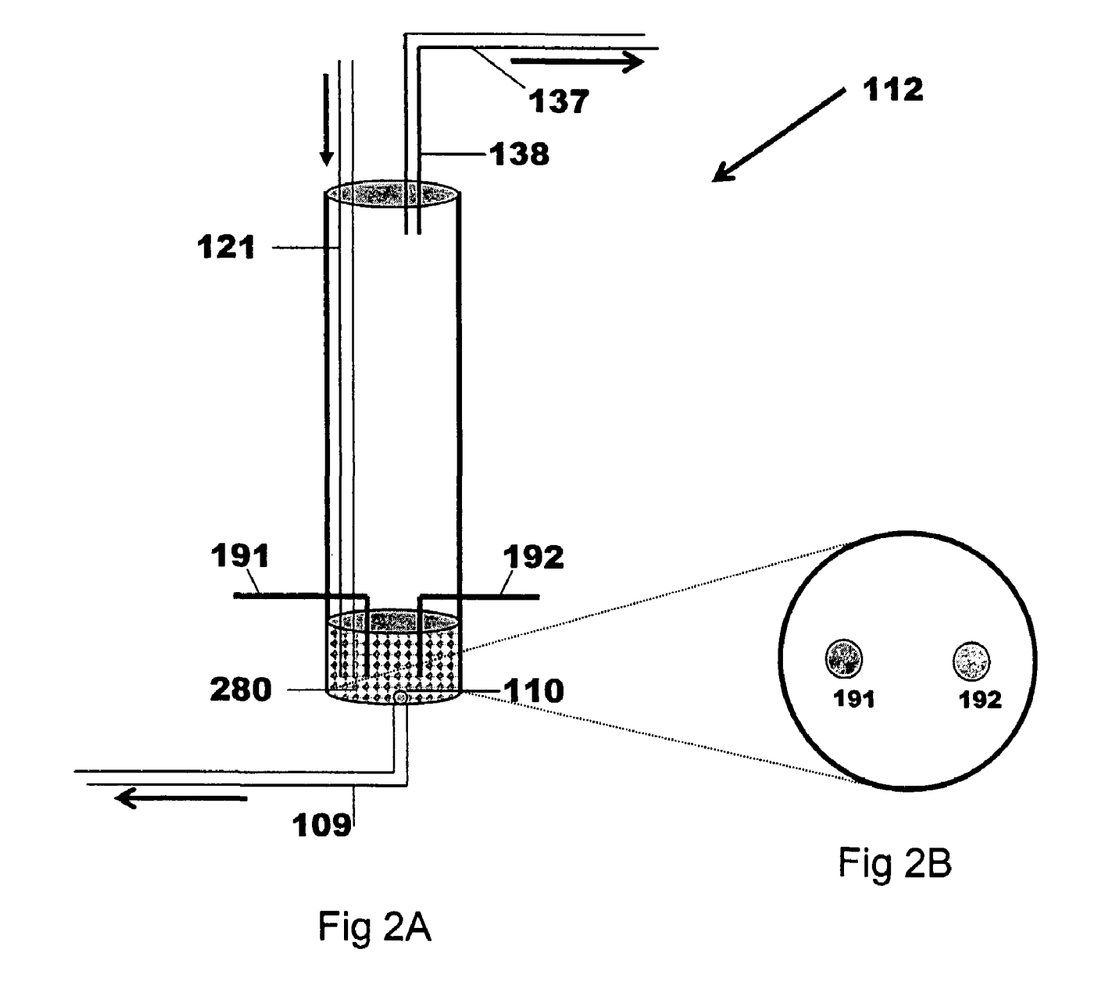
FIG. 2A is an illustration of an electrolytic apparatus, in accordance with an embodiment of the present invention.
FIG. 2B is a view of two electrodes in the electrolytic apparatus of FIG. 2A.

FIGS. 2A and 2B in conjunction with FIG. 1 show electrolytic apparatus 112 including a reservoir for receiving solution sample 280 and the electrodes used for electrolysis. In one example, with no intent to limit the invention thereby, the reservoir of electrolytic apparatus 112 is made of Kel-F to provide compatibility with various solutions without leaching of contaminants. However, reservoirs of various shape and material are applicable which provide a sufficient inert characteristic with various solutions.

In one example, with no intent to limit the invention thereby, the two electrodes 191 and 192 are platinum metal rods. Power is applied to electrodes 191 and 192 by a polarity switching apparatus 154.

Figure 2C:
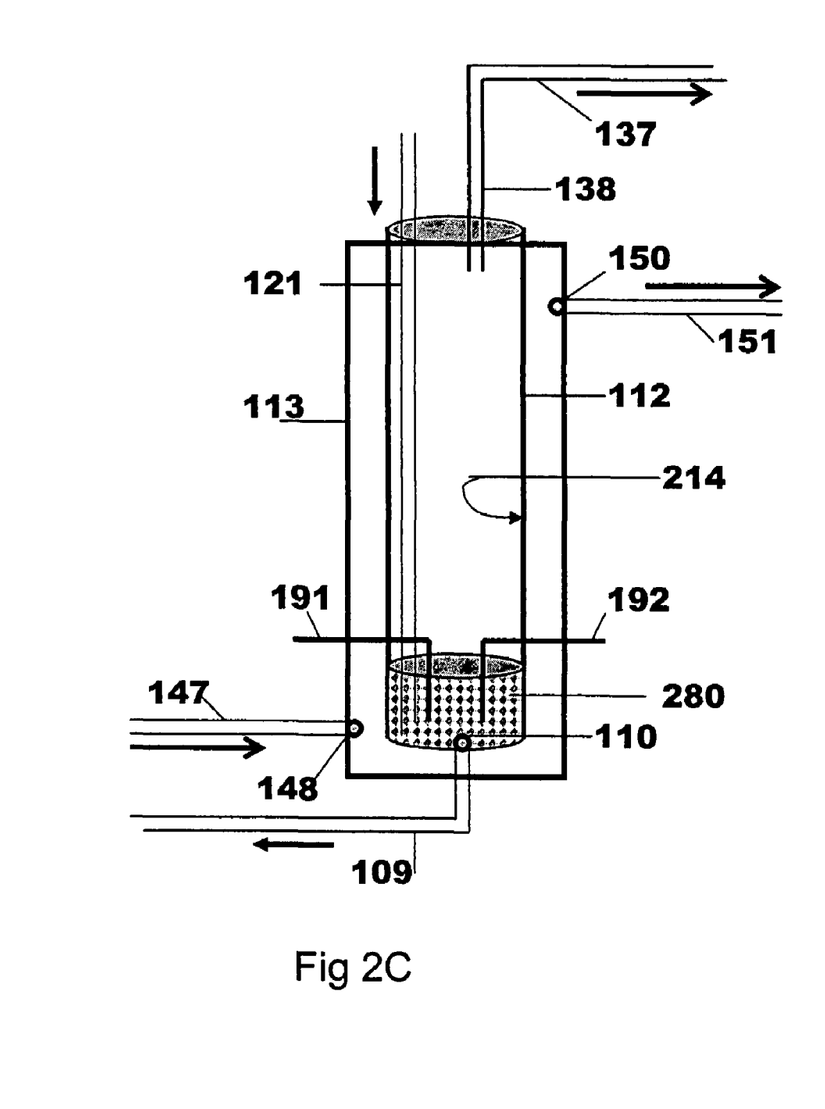
FIG. 2C shows the electrolytic apparatus of FIG. 2A enclosed in a cooling jacket, in accordance with an embodiment of the present invention.

Referring now to FIG. 2C in conjunction with FIG. 1, a cooling solution may be sent through an outer jacket 113 of electrolytic apparatus 112 when electrolytic apparatus 112 is in use. As the electrolysis progresses, the sample becomes less conductive and more resistive because of the depletion of ionic species, and consequently the temperature of the solution sample increases over time. It is desirable to keep the sample temperature low so that some of the highly volatile metals do not evaporate. To achieve this goal, a cooling solution is moved through cooling jacket 113 wrapped around electrolytic apparatus 112. The cooling solution is sent through line 143 (FIG. 1) and micro-metering valve 144 (FIG. 1), which sets the flow rate of the cooling solution. Shut-off valve 146 (FIG. 1) is used to stop the flow of cooling solution when electrolytic apparatus 112 is not in use. The cooling solution then flows through line 147 and into a cooling solution input port 148 of outer jacket 113 and exits through an output port 150. A line 151 transports the spent cooling solution to a drain 152 (FIG. 1) for disposal. In one example, with no intent to limit the invention thereby, clean water is used for cooling solution. In a further example, with no intent to limit the invention thereby, metering valve 144 is a valve having part number P-445, and check valve 146 is a valve having part number CV-3000, both available from Upchurch Scientific of Oak Harbor, Wash.

Figure 3:
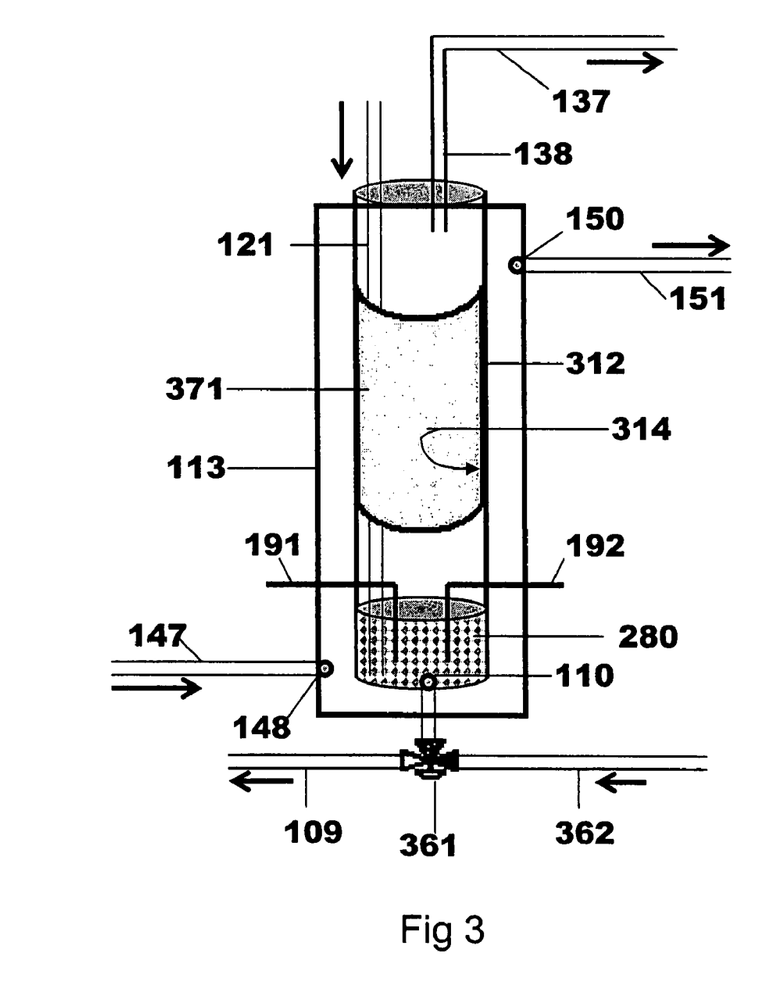
FIG. 3 shows a block diagram of an electrolytic apparatus including a nitrogen gas line and a vibrator for agitation of the solution, in accordance with an embodiment of the present invention.

Referring now to FIG. 3, the agitation of solution during electrolysis is important to expedite the decomposition of the matrix. Most of the agitation is accomplished by the formation of gaseous bubbles produced during electrolysis. This phenomenon is further enhanced by changing the polarity of the electrodes as will be discussed in greater detail below. As the solution sample becomes more and more diluted as electrolysis progresses, the formation of gases is also reduced. Thus, the agitation by gaseous bubbles is reduced. It is observed that an external source of agitation improves and expedites the decomposition of a matrix. In one example, with no intent to limit the invention thereby, nitrogen gas is bubbled through the solution sample via line 362 and valve 361 to further increase the agitation of solution during the electrolysis. Advantageously, the bubbling of nitrogen gas can also help to push byproduct gas (e.g., chlorine gas) out of the electrolytic apparatus to help decrease the formation of undesirable products from reaction with the byproduct gas (e.g., hypochlorous acid).

In a further example, agitation of the solution sample can be achieved by periodically circulating the solution from electrolytic cell 112 to syringe 108 through valve 116 and valve stack 106. This process can be accomplished by stopping the electrolysis for a few seconds and then pulling the sample into syringe 108. This process also helps to clean residual matrix from the lining, valves, and syringe 108. In one example, 2 ml of solution sample including SC2 is electrolyzed for 30 minutes. Every 5 minutes during the electrolysis, the process is stopped for 23 seconds and the sample is pulled into syringe 108 and then pushed back to electrolytic apparatus 112. The 2 ml of sample is pulled into syringe 108 in about 10 seconds, remains in syringe 108 for about 3 seconds, and then is pushed back into electrolytic apparatus 112 in about 10 seconds.

Referring again to FIG. 3, during the electrolysis, water vapor condenses on the inner surface 314 of electrolytic apparatus 312, and gases are produced that bubble out of the solution sample and come in contact with the condensed water vapor so as to be re-dissolved. As electrolysis progresses, more and more gas molecules dissolve in the condensed water vapor and may ultimately form a highly concentrated matrix that may never be electrolyzed. In one example, when chlorine gas bubbles out of SC2 solution, the chlorine gas re-dissolves in water vapor condensed on inner surface 314 of electrolytic apparatus 312 and forms strong hydrochloric acid. Thus, the removal of water vapor and hydrochloric acid from the inner surface of electrolytic apparatus 312 becomes desirable. In one example, an external vibrator 371 can be used to physically shake electrolytic apparatus 312 so as to dislodge the condensed water vapor (or matrix) back into the solution. In one example, with no intent to limit the invention thereby, external vibrator 371 may be a cylindrical piezoceramic vibrator that is adapted to wrap around electrolytic apparatus 312.

As previously mentioned in one example, the decomposition of SC2 produces chlorine gas in electrolytic apparatus 112. Referring back to FIG. 1, chlorine gas is taken out of electrolytic apparatus 112 by applying suction to a scrubbing solution container 134 operably coupled to electrolytic apparatus 112. Chlorine gas passes through line 138, line 137, valve 136, and line 135 to scrubbing solution container 134. As illustrated in FIG. 1, the end of line 135 is submerged in the scrubbing solution to dissolve the chlorine gas in solution, in one example forming hydrochloric acid in water. Thus, the harmful gaseous byproduct of chlorine gas may be safely removed from the electrolytic apparatus.

It is noted that lines transporting solution sample, cooling solution, or gaseous byproducts may comprise piping, fittings, and/or tubing in one example, but any applicable material and structure that allows for the accurate transfer of liquids and/or gases may be used to operably connect to valves, syringes, reservoirs, and other parts in accordance with the present invention. In one example, with no intent to limit the invention thereby, components are connected with tubing made of Teflon® PFA 450 HP fluoropolymer, having 0.062" O.D.×0.016" I.D., Part #106-0062016, available from Parker Hannifin of Cleveland, Ohio.

Figure 4:
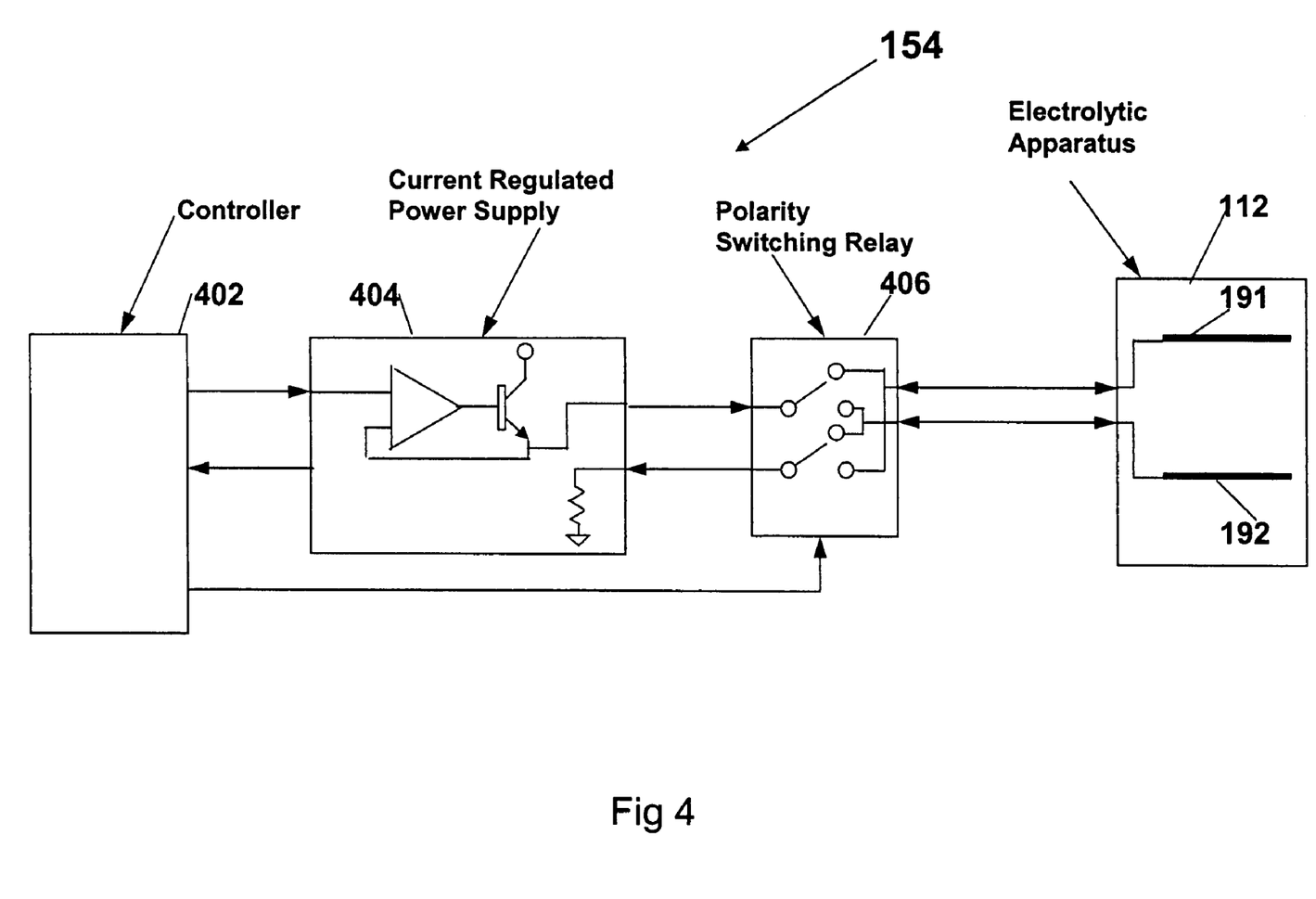
FIG. 4 is a block diagram of a polarity switching apparatus including a controller, a power supply, and a reverse polarity switching relay coupled to an electrolytic apparatus, in accordance with an embodiment of the present invention.

Referring now to FIG. 4, a block diagram of a polarity switching apparatus 154 is illustrated, including a controller 402, a power supply 404, and a reverse polarity switching relay 406 operably coupled to electrolytic apparatus 112, in accordance with an embodiment of the present invention.

A microprocessor-based controller 402, with either discrete or serial communication, and analog or digital control, applies an operator-selected current set point to a current regulated power supply 404. Actual current and voltage feedback may be monitored by controller 402 for diagnostic purposes. The desired current is set by controller 402 to achieve optimum decomposition rate. In one example, with no intent to limit the invention thereby, controller 402 includes a Contec PR105 Chassis, ACE 870 Power Supply, IP5S2 Passive Backplane, PCISA-3716 Single Board Computer, plus Measurement Computing DAS1002, available from Automation and Control Products of San Jose, Calif.

Current regulated power supply 404 provides either regulated DC or PW controlled DC average current to reverse polarity switching relay 406. In one example, with no intent to limit the invention thereby, power supply 404 is a model PWR-2A available from Merobel of France.

Reverse polarity switching relay 406 receives current from current regulated power supply 404 and switches direction of current supplied to electrodes 191 and 192 of electrolytic apparatus 112 at the command of microprocessor controller 402. In one example, with no intent to limit the invention thereby, reverse polarity switching relay 406 is a model RH2B-UL available from IDEC Corporation of Japan.

Figure 5:
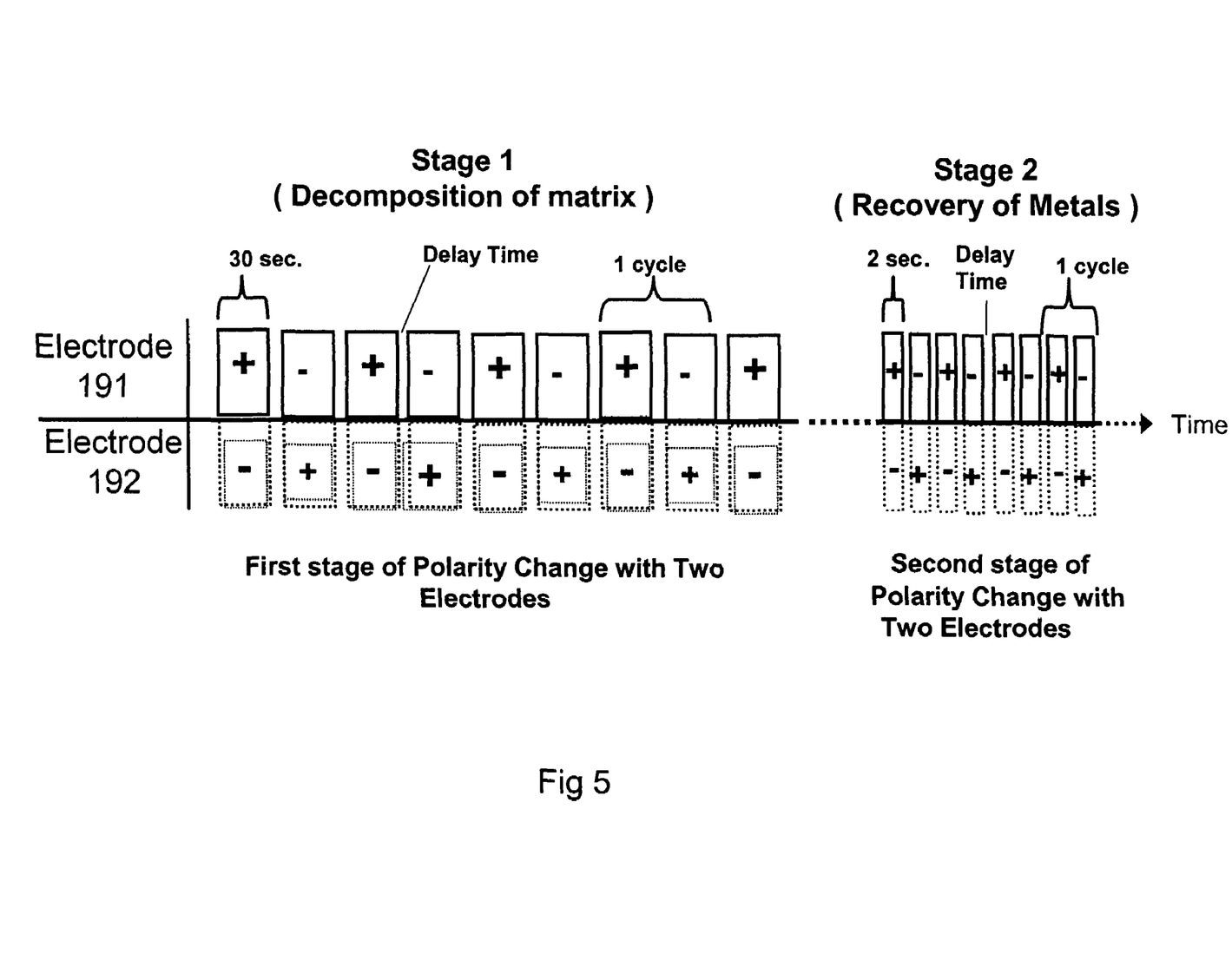
FIG. 5 is an illustration of first and second stages of polarity reversal with two electrodes, in accordance with an embodiment of the present invention.

Referring now to FIG. 5 in conjunction with FIG. 1, a method of trace metal analysis including electrolysis and metals recovery will be explained in greater detail. A process in accordance with the present invention is shown as a two stage process: the first stage includes decomposing the matrix; and the second stage includes recovering deposited or precipitate metals and stabilizing the metals in solution. When electrical potential (i.e., voltage) is applied between electrodes 191 and 192, the ions in the sample matrix are attracted toward their oppositely charged electrode. In one example, when SC2 sample matrix ($HCl/H_2O_2/H_2O$) is electrolyzed, the chloride ions ($Cl^-$) are attracted toward the anode (+), and cation metals ($M^+$) are attracted toward the cathode (−). At the anode, chloride ions are oxidized and form chlorine gas while at the cathode, water is reduced to form hydrogen gas.

The main reactions are shown in equation form below:

$$2Cl^- - 2e^- ===> Cl_2 \text{ (at the anode)}$$

$$2H_2O + 2e^- ===> 2OH^- + H_2 \text{ (at the cathode)}$$

Side reactions are shown in equation form below:

$$H_2O_2 ===> O_2 + 2H^+ + 2e^- \text{ (at the anode)}$$

$$2H_2O ===> O_2 + 4H^+ + 4e^- \text{ (at the anode)}$$

$$H_2O_2 + 2H^+ + 2e^- ===> 2H_2O \text{ (at the cathode)}$$

In the case of the SC2 sample matrix, a major portion of the chlorine gas is bubbled off and pulled away through line 138 (FIG. 1). A portion of the chlorine gas produced at the anode is dissolved in water and forms hypochlorite ($HOCl + ClO^-$), which is a very strong oxidizing agent.

The reaction is shown in equation form below:

$$Cl_2 + 2H_2O \Longleftrightarrow HClO + Cl^- + H_3O^+ \text{ (Hypochlorous acid)}$$

$$HClO + H_2O \Longleftrightarrow ClO^- + H_3O^+ \text{ (Hypochlorite ion)}$$

The high concentration of hypochlorite may cause the deterioration of platinum electrodes.

While decomposition of the SC2 matrix to chlorine gas occurs at the anode, metals are reduced at the cathode and are deposited onto the electrode. To keep the metals in solution and to minimize the hypochlorite concentration, the polarity of the voltages applied to electrodes 191 and 192 is symmetrically reversed at set time intervals (i.e., the polarity of each electrode is changed, e.g., reversed, as a function of time as shown by the plus and minus signs). The passage of time is indicated by the arrow marked "time".

In one example, electrode 191 is initially at a positive potential and electrode 192 is initially at a negative potential for a time interval of 30 seconds. After a one second delay, electrode 192 is switched to a positive potential and electrode 191 is switched to a negative potential for a time interval of 30 seconds. This cycle of reversed polarity, with one cycle occurring after both a positive and a negative charge (or a negative and a positive charge) have been applied to an electrode, occurs fifteen (15) times in one example during a first stage of potential or voltage application for SC2 matrix decomposition. At the end of 15 reversed polarity cycles, a second stage of reversed polarity cycles occurs with an electric potential application of two seconds duration (i.e., time interval) and a one second delay between the polarity changes. The second stage of polarity switching lasts for five (5) cycles in one example. During this second stage, metals are stabilized in solution and also stripped from both electrodes and dissolved into the solution. The treated sample is passed into syringe 108 (FIG. 1) and injected to analyzer 132 (FIG. 1) for metals detection and analysis.

Figure 6A:
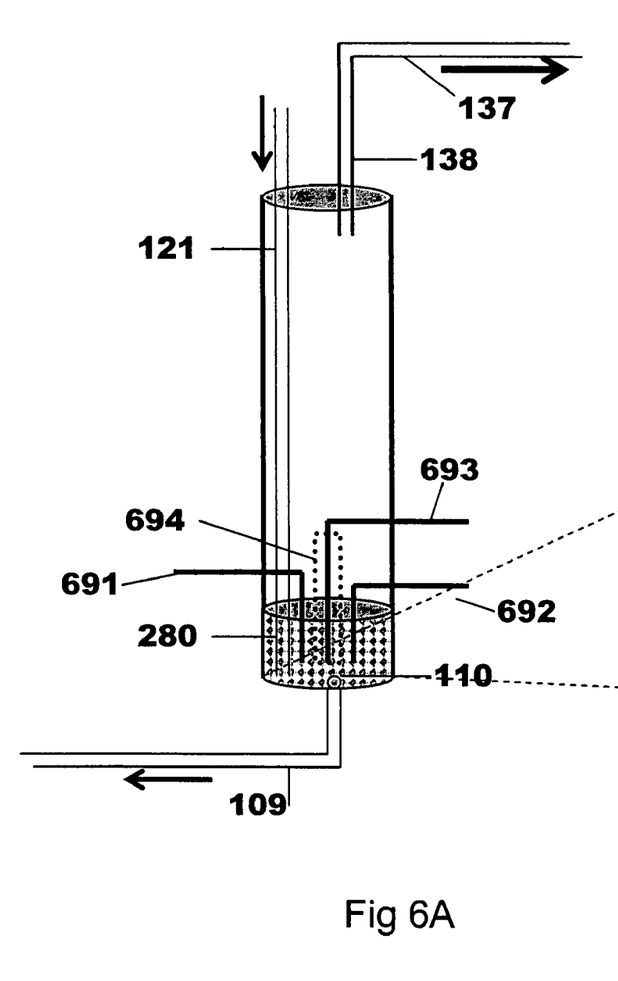
FIG. 6A shows an electrolytic apparatus with three electrodes, in accordance with an embodiment of the present invention.
Figure 6B:
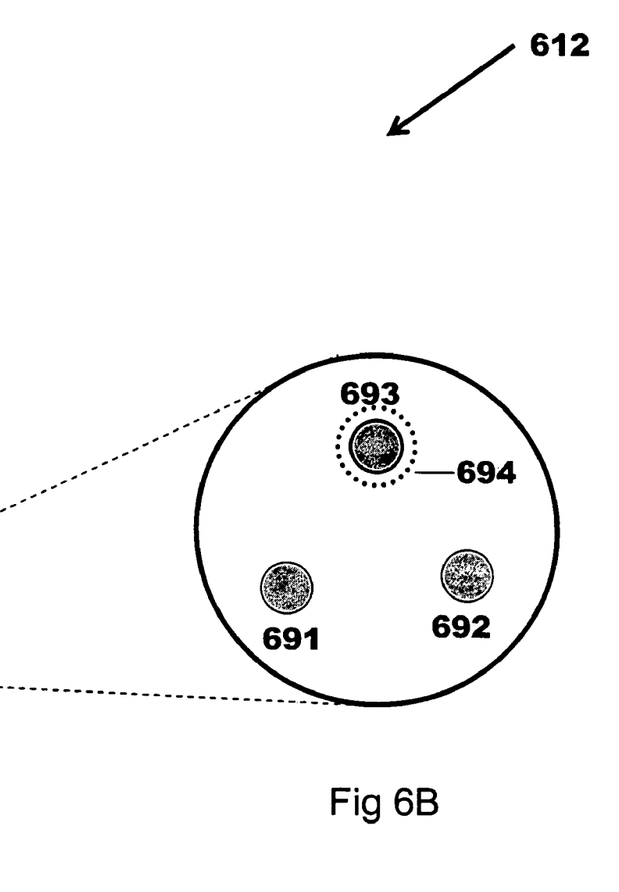
FIG. 6B is a view of the three electrodes in the electrolytic apparatus of FIG. 6A.
Figure 7:
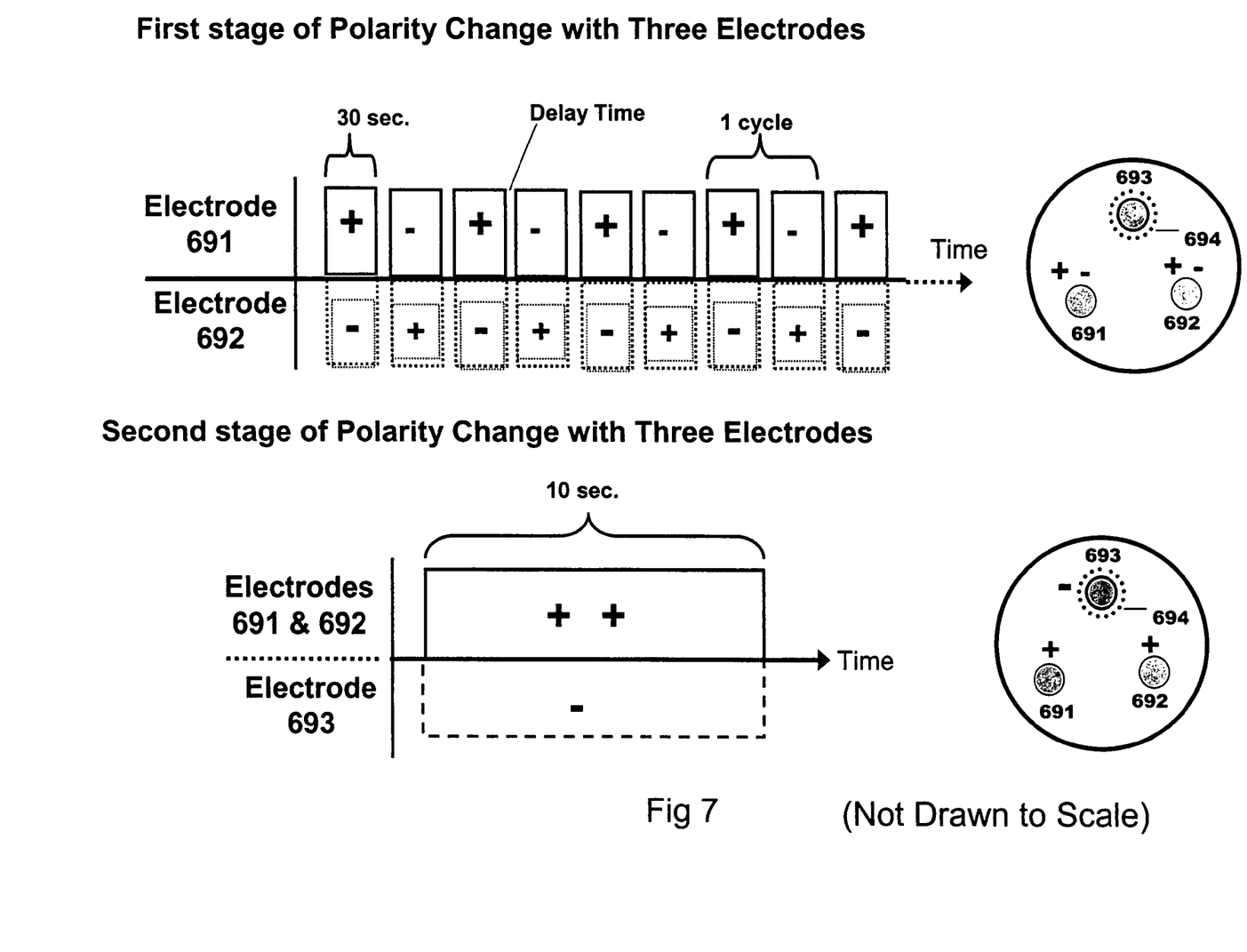
FIG. 7 is an illustration of first and second stages of polarity reversal with three electrodes, in accordance with an embodiment of the present invention.

FIGS. 6A and 6B in conjunction with FIG. 7 illustrate another embodiment of the present invention. Instead of only two electrodes (e.g., electrodes 191 and 192 in FIGS. 1-5), three electrodes 691, 692, and 693 are placed in the solution sample. At least the portion of electrode 693 in contact with the solution sample is covered with an anion exchange membrane 694. In one example, first stage polarity switching is executed between electrode 691 and electrode 692 as explained above with regard to electrodes 191 and 192. During the second stage, electrode 691 and electrode 692 are kept at a positive potential and electrode 693 is kept at a negative potential. In this example, metals are stripped from both electrodes 691 and 692 simultaneously, and the stripped metals are attracted toward electrode 693 but are prevented from reaching the surface of electrode 693 by an anion exchange membrane 694. Thus, the metal ions remain in solution for subsequent analysis.

The method and apparatus of the present invention can be utilized as a stand alone module or can be incorporated with sampling and analytical instruments. In one example, the electrolytic apparatus and method of the present invention may be integrated with a "Trace Contamination Analyzer" (TCA) or a "Chemical Constituents Analyzer" (CCA), both available from Metara Inc. of Sunnyvale, Calif.

Advantageously, in one embodiment, the entire operation, from extracting the sample to mixing an internal standard to treating the sample by electrolysis (i.e., decomposing or neutralizing the matrix and recovering metals in solution), followed by sample analysis, is online, automated, and controlled by computer. In the beginning of an analysis process, a "job" is built by selecting the type of matrix being investigated and its concentration, for example SC2. Then the variable parameters, such as the sample volume, electrolytic current, first stage polarity change time, first stage delay, first stage number of cycles, second stage polarity change time, second stage delay, and second stage number of cycles, are selected. Other variable parameters, such as agitation cycle, duration, and frequency, may be entered and controlled via computer.

Figure 8:
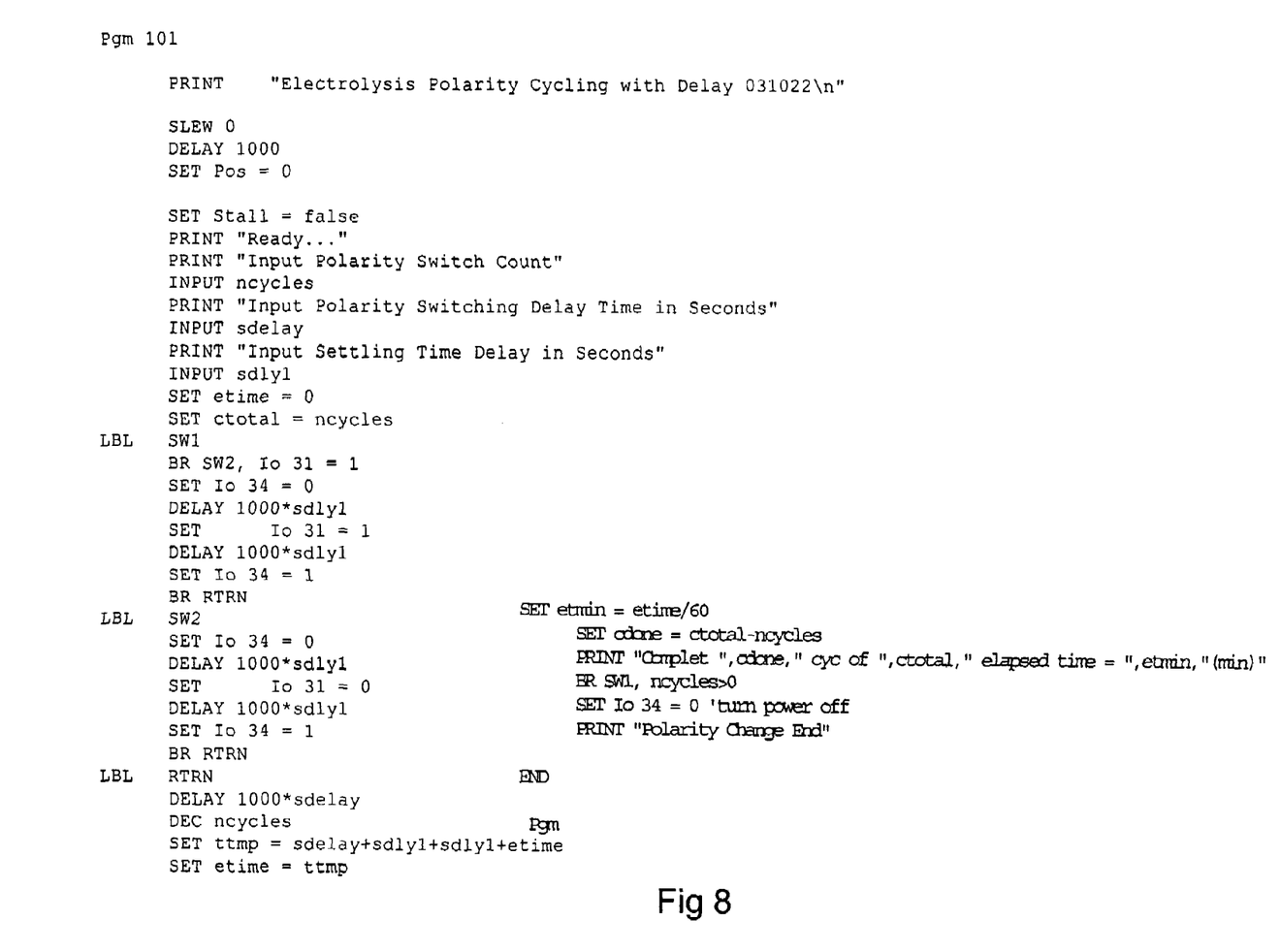
FIG. 8 is an example of a configuration file for operating an apparatus for analyzing trace metals, in accordance with an embodiment of the present invention.

An example of an electrolytic apparatus configuration file is shown in FIG. 8. In this example, the electrolytic configuration file is an ASCII text file, editable in any text editor, which contains configuration parameters that instruct software how to operate the hardware. The solution matrix and concentration is the primary criteria. In one example, the software can include software entitled "Job Scheduler" available from Metara Inc. of Sunnyvale, Calif. The file is read and parsed by the Metara Job Scheduler with C++ classes (Microsoft® CString and CFile classes).

Figure 9:
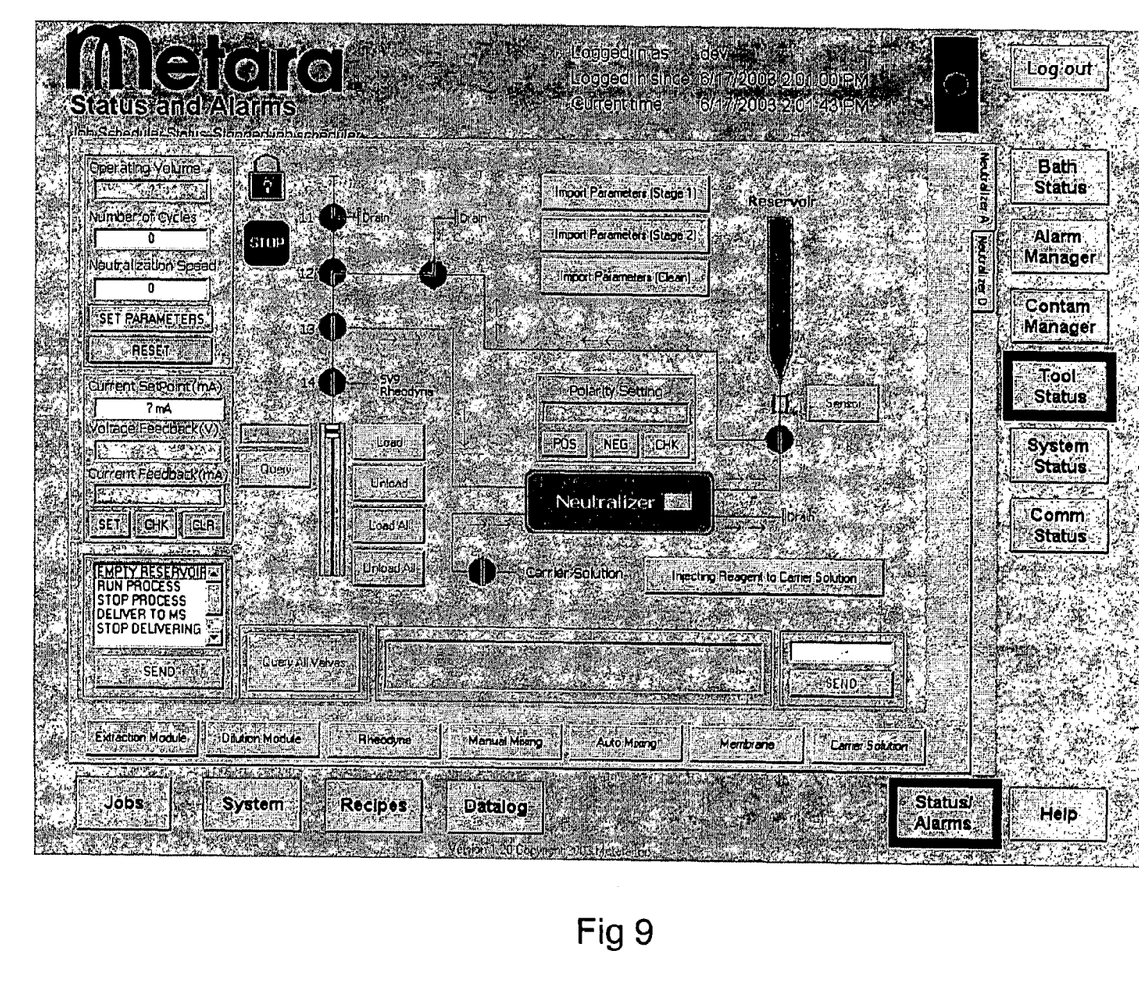
FIG. 9 is a screen shot from a computer controlling an apparatus for analyzing trace metals, in accordance with an embodiment of the present invention.

FIG. 9 shows an example of a potential screen shot from the computer controlling the electrolysis apparatus utilizing the Metara Job Scheduler in accordance with an embodiment of the present invention. Thus, computer software may automatically select the concentration and composition of cooling solution depending on the nature of the matrix.

In one example, when the electrolytic apparatus of the present invention is integrated with TCA to analyze metallic contaminants in a semiconductor processing bath, the following sequence of operations may be executed.

The "initializing dilution module hardware" operation cleans any residual standard left from a previous run and fills the syringes with fresh standard solution.

The "initializing mix module" operation cleans the mixing reservoirs and syringes where sample will be mixed with the standard.

The "cleaning electrolytic cell" operation cleans the residual sample from cell with UPW first and then with air.

In the mean time, the "sample extraction module" operation is initialized and the recipe of the job is loaded for execution.

After these operations, the apparatus of the present invention performs treatment of a solution sample to decompose the matrix and stabilize the metals in solution in accordance with the methods described above. Finally, the sample is delivered to an analytical instrument for analysis, such as an electro spray mass spectrometer (ES-MS), an inductively coupled plasma mass spectrometer (ICP-MS), an atomic absorption spectrometer (AAS), or a liquid chromatograph (LC), which utilize the concepts of mass spectroscopy, inductively coupled plasma mass spectrometry, atomic absorption spectroscopy, and liquid chromatography, respectively. It will be apparent that various analytical devices may be used within the scope of the present invention.

Two experiments which were conducted utilizing a method and apparatus of the present invention will now be described.

EXAMPLE 1

30 milliliters of SC2 solution (HCl:$H_2O_2$:$H_2O$ at ratio 1:1:6) was spiked with a known amount of metals in the range of 1-5 part per billion (ppb). The solution was divided into three equal parts. Five equal samples from each part (i.e., 2 milliliters of spiked SC2 solution) were separately electrolyzed under similar conditions in an electrolytic apparatus having two rod-shaped electrodes. The total surface area of each electrode was 0.225 cm$^2$, and the current at the start of electrolysis was 1.5 amperes at 6 volts.

For the first set of samples, no polarity was reversed during 30 minutes of electrolysis. The second set of samples was electrolyzed with only a first stage of voltage application including electrolysis duration for a time interval of 30 seconds and 1 second delay between polarity reversal for 15 cycles, one cycle occurring after both a positive and a negative charge (or a negative and a positive charge) have been applied to an electrode. The third set of samples was electrolyzed with first and second stages of voltage application, the first stage including electrolysis duration for a time interval of 30 seconds and a 1 second delay between polarity reversal for 15 cycles, and the second stage including electrolysis duration of 2 seconds with a 1 second delay between polarity reversal for 5 cycles. After the electrolysis, the three sets of samples were analyzed by an Electro-spray Ion Trap Time of Flight Mass Spectrometer (ES-MS). Other apparatus and methods of analysis could also have been used, for example by ICP-MS, AAS, or LC.

The average percentage metals recovery was calculated from the raw data based upon ES-MS signal intensity and are shown in Table 1 below. The results show that metal recovery was relatively poor for the first set of samples where no polarity was changed. The second set of samples with a first stage of polarity change showed a higher percentage recovery as compared to the first set of samples. The third set of samples with first and second stages of voltage application showed the highest percentage metals recovery as compared to the other sets of samples.

TABLE 1

| Experimental Set | Avg. Percentage of Metal Recovery (%) | | |
|---|---|---|---|
| | Cr53 | Ni62 | Zn68 |
| (1) No Polarity Change | 11 | 28 | 33 |
| (2) First Stage of Polarity Change | 53 | 58 | 57 |
| (3) First and Second Stages of Polarity Change | 69 | 70 | 80 |

EXAMPLE 2

In another example, fresh 30 milliliter of SC2 solution (HCl:H$_2$O$_2$:H$_2$O ratio 1:1:6) was spiked with a known amount of metals in the range of 1-5 part per billion (ppb). The solution was divided into three equal parts. Five equal samples from each part (i.e., 2 milliliter of spiked SC2 solution) were separately electrolyzed under similar conditions in the same electrolytic cell as in Example 1. The three sets of samples were electrolyzed with first and second stages of voltage application including electrolysis duration of 30 seconds and a 1 second delay between polarity reversal for 15 cycles during the first stage. For the first set of samples, during the second stage when metal recovery occurs, electrolysis duration was about ½ second with a 1 second delay between polarity reversal for 5 cycles. The second set of samples was electrolyzed with a second stage of voltage application including electrolysis duration of 1 second with a 1 second delay between polarity reversal for 5 cycles. The third set of samples was electrolyzed with a second stage of voltage application including electrolysis duration of 2 seconds with a 1 second delay between polarity reversal for 5 cycles. After the electrolysis, the three sets of samples were analyzed by an ES-MS, and the average percentage metals recovery was calculated from the raw data based upon ES-MS signal intensity. Again, as noted above, other apparatus and methods of analysis could have been used.

Table 2 below shows that metals recovery was relatively poor for the first set of samples that included a total of 5 seconds (10 times×½ second) of metals recovery time. The second set of samples that included 10 seconds (10 times×1 second) of metals recovery time showed a relatively higher or similar percentage recovery as compared to the first set of samples. The third set of samples with 20 seconds (10 times×2 seconds) of metals recovery time showed the highest percentage metals recovery as compared to the other sets of samples.

TABLE 2

| Experimental Set | Avg. Percentage of Metal Recovery (%) | | | | |
|---|---|---|---|---|---|
| | K39 | Ca44 | Ti46 | Cr53 | Co59 |
| (1) ½ sec, 10 times | 63 | 41 | 49 | 83 | 50 |
| (2) 1 sec, 10 times | 61 | 44 | 66 | 78 | 46 |
| (3) 2 sec, 10 times | 119 | 82 | 80 | 110 | 70 |

No baseline subtraction was calculated into the data, thereby resulting in some metals having a percentage recovery greater than 100%. Typically, a blank or standard is analyzed prior to, subsequent to, or substantially simultaneously with the solution sample for baseline subtraction/calibration.

The above-described embodiments of the present invention are merely meant to be illustrative and not limiting. Various changes and modifications may be made without departing from this invention in its broader aspects. Therefore, the appended claims encompass all such changes and modifications as falling within the true spirit and scope of this invention.

What is claimed is:

1. A method of analyzing trace metals in solution, comprising:
   providing a first electrode and a second electrode in a reservoir;
   providing a sample in the reservoir so that the sample is in contact with the first and second electrodes, the sample including a matrix and at least one trace metal to be analyzed;
   applying a first stage voltage to the first electrode and applying a first stage voltage of opposite polarity to the second electrode, wherein the polarity of the first stage voltages are repeatedly reversed at a first time interval and for a first number of cycles to thereby decompose the matrix; and
   applying a second stage voltage to the first electrode and applying a second stage voltage of opposite polarity to the second electrode, wherein the polarity of the second stage voltages are repeatedly reversed at a second time interval and for a second number of cycles to thereby stabilize the at least one trace metal in solution for subsequent analysis.

2. The method of claim 1, wherein the at least two electrodes include an anode and a cathode.

3. The method of claim 1, wherein the matrix includes a solution of hydrochloric acid (HCl), hydrogen peroxide ($H_2O_2$), and water.

4. The method of claim 1, wherein the first time interval is about 30 seconds.

5. The method of claim 1, wherein the first number of cycles is about 15.

6. The method of claim 1, further comprising providing a time delay between the reversing of the polarity of the first stage voltages.

7. The method of claim 6, wherein the time delay is about 1 second.

8. The method of claim 1, wherein the second time interval is about 2 seconds.

9. The method of claim 1, wherein the second number of cycles is about 5.

10. The method of claim 1, further comprising providing a time delay between the reversing of the polarity of the second stage voltages.

11. The method of claim 10, wherein the time delay is about 1 second.

12. The method of claim 1, further comprising analyzing the at least one trace metal by mass spectroscopy, inductively coupled plasma mass spectrometry, atomic absorption spectroscopy, or liquid chromatography.

13. The method of claim 1, further comprising cooling the sample during application of voltages to the first and second electrodes.

14. The method of claim 1, further comprising agitating the sample during application of voltages to the first and second electrodes.

15. The method of claim 1, further comprising removing gaseous byproducts from the decomposed matrix.

16. A method of analyzing trace metals in solution, comprising:
    providing a first electrode, a second electrode, and a third electrode in a reservoir;
    providing a sample in the reservoir so that the sample is in contact with the first, second, and third electrodes, the sample including a matrix and at least one trace metal to be analyzed;
    applying a first stage voltage to the first electrode and applying a first stage voltage of opposite polarity to the second electrode, wherein the polarity of the first stage voltages are repeatedly reversed at a first time interval and for a first number of cycles to thereby decompose the matrix; and
    applying a second stage voltage to the first and second electrodes and applying a second stage voltage of opposite polarity to the third electrode to thereby stabilize the at least one trace metal in solution for subsequent analysis.

17. The method of claim 16, wherein the matrix includes a solution of hydrochloric acid (HCl), hydrogen peroxide ($H_2O_2$), and water.

18. The method of claim 16, wherein the first time interval is about 30 seconds.

19. The method of claim 16, wherein the first number of cycles is about 15.

20. The method of claim 16, further comprising providing a time delay between the reversing of the polarity of the first stage voltages.

21. The method of claim 20, wherein the time delay is about 1 second.

22. The method of claim 16, wherein the second stage voltages are applied for about 10 seconds.

23. The method of claim 16, further comprising surrounding at least the portion of the third electrode in contact with the sample with an anion exchange membrane.

24. The method of claim 16, further comprising analyzing the at least one trace metal by mass spectroscopy, inductively coupled plasma mass spectrometry, atomic absorption spectroscopy, or liquid chromatography.

25. The method of claim 16, further comprising cooling the sample during application of voltages to the first, second, or third electrodes.

26. The method of claim 16, further comprising agitating the sample during application of voltages to the first, second, or third electrodes.

27. The method of claim 16, further comprising removing gaseous byproducts from the decomposed matrix.

* * * * *